(12) United States Patent
Choi et al.

(10) Patent No.: US 9,192,485 B2
(45) Date of Patent: Nov. 24, 2015

(54) TISSUE PROSTHESIS INSERTION SYSTEM AND METHOD

(71) Applicant: SPINECELL PARTY, LTD, Kogarah (AU)

(72) Inventors: Johnathon Choi, Carlingford (AU); Zoran Milijasevic, Bayview Heights (AU); Ashish Dhar Diwan, Sydney (AU)

(73) Assignee: SPINCELL PRIVATE LTD

( * ) Notice: Subject to any disclaimer, the term of this patent is extended or adjusted under 35 U.S.C. 154(b) by 45 days.

(21) Appl. No.: 14/275,041

(22) Filed: May 12, 2014

(65) Prior Publication Data

US 2014/0249634 A1    Sep. 4, 2014

Related U.S. Application Data

(62) Division of application No. 12/740,651, filed as application No. PCT/AU2007/001657 on Oct. 31, 2007, now Pat. No. 8,728,161.

(51) Int. Cl.

| | |
|---|---|
| *A61F 2/44* | (2006.01) |
| *A61M 5/00* | (2006.01) |
| *A61F 2/46* | (2006.01) |
| A61F 2/30 | (2006.01) |
| A61M 5/19 | (2006.01) |

(52) U.S. Cl.
CPC ............... *A61F 2/4601* (2013.01); *A61F 2/441* (2013.01); *A61F 2/4611* (2013.01); *A61F 2002/30069* (2013.01); *A61F 2002/30079* (2013.01); *A61F 2002/30235* (2013.01); *A61F 2002/30583* (2013.01); *A61F 2002/30601* (2013.01); *A61F 2002/444* (2013.01); *A61F 2002/4685* (2013.01); *A61F 2210/009* (2013.01); *A61F 2210/0085* (2013.01); *A61F 2230/0069* (2013.01); *A61M 5/19* (2013.01)

(58) Field of Classification Search
CPC .......... A61M 5/145; A61M 5/19; A61M 5/14
USPC ....................... 623/17.11–17.16; 604/83, 191
See application file for complete search history.

(56) References Cited

U.S. PATENT DOCUMENTS

| | | | | |
|---|---|---|---|---|
| 5,489,256 | A * | 2/1996 | Adair ................. | A61B 1/00073 600/123 |
| 5,492,538 | A * | 2/1996 | Johlin, Jr. .......... | A61M 25/0068 128/899 |
| 5,643,175 | A * | 7/1997 | Adair ................. | A61B 1/00073 600/123 |
| 6,030,415 | A * | 2/2000 | Chuter ..................... | A61F 2/07 604/191 |

(Continued)

*Primary Examiner* — Eduardo C Robert
*Assistant Examiner* — Stuart S Bray
(74) *Attorney, Agent, or Firm* — Jerry R. Potts; James R. McDaniel

(57) ABSTRACT

A tissue prosthesis insertion system (80) includes a first assembly (10) comprising a plurality of nested tubes (12), one of the tubes being a carrier tube (14) which, in use, receives a component (16) of a tissue prosthesis at a distal end of the carrier tube (14). A magnetic mount (44) is carried at a proximal end of the first assembly (10). A second assembly (82) is removably attachable to the first assembly (10). An attachment device (92) is carried at a distal end of the second assembly (92), the attachment device (92) being responsive to the magnetic mount (44) of the first assembly (10), the magnetic mount (44) and the attachment device (92) carrying complementary engaging formations to facilitate hermetic sealing between the magnetic mount (44) and the attachment device (92).

20 Claims, 4 Drawing Sheets

(56) References Cited

U.S. PATENT DOCUMENTS

| | | | | |
|---|---|---|---|---|
| 6,059,719 | A * | 5/2000 | Yamamoto | A61B 1/00059 600/104 |
| 6,065,371 | A * | 5/2000 | Yacowitz | A61M 37/0076 30/362 |
| 6,079,868 | A * | 6/2000 | Rydell | A61B 17/00234 222/145.6 |
| 6,705,756 | B2 * | 3/2004 | Botrie | B01F 5/0613 222/136 |
| 7,077,339 | B2 * | 7/2006 | Leach | A61B 17/00491 222/137 |
| 7,316,704 | B2 * | 1/2008 | Bagaoisan | A61B 17/0057 606/213 |
| 7,960,935 | B2 * | 6/2011 | Farritor | A61B 1/00156 318/568.11 |
| 2001/0004710 | A1 * | 6/2001 | Felt | A61B 17/7097 623/17.12 |
| 2003/0018390 | A1 * | 1/2003 | Husson | A61B 17/3201 623/17.16 |
| 2004/0024465 | A1 * | 2/2004 | Lambrecht | A61B 5/1076 623/17.16 |
| 2004/0044412 | A1 * | 3/2004 | Lambrecht | A61B 5/1076 623/17.16 |
| 2005/0043806 | A1 * | 2/2005 | Cook | A61B 17/15 623/20.12 |
| 2006/0004326 | A1 * | 1/2006 | Collins | A61B 17/8811 604/57 |
| 2006/0084983 | A1 * | 4/2006 | Kim | A61B 17/7065 606/914 |
| 2006/0247776 | A1 * | 11/2006 | Kim | A61F 2/442 623/17.12 |
| 2006/0265077 | A1 * | 11/2006 | Zwirkoski | A61B 17/7094 623/17.16 |
| 2006/0270781 | A1 * | 11/2006 | Ruberti | A61F 2/442 524/503 |
| 2006/0276802 | A1 * | 12/2006 | Vresilovic | A61F 2/4657 606/102 |
| 2006/0287726 | A1 * | 12/2006 | Segal | A61F 2/441 623/17.12 |
| 2006/0287727 | A1 * | 12/2006 | Segal | A61F 2/441 623/17.12 |
| 2006/0287729 | A1 * | 12/2006 | Segal | A61F 2/441 623/17.16 |
| 2006/0287730 | A1 * | 12/2006 | Segal | A61F 2/441 623/17.16 |
| 2006/0293750 | A1 * | 12/2006 | Sherman | A61F 2/44 623/17.12 |
| 2007/0123986 | A1 * | 5/2007 | Schaller | A61B 17/70 623/17.11 |
| 2007/0162135 | A1 * | 7/2007 | Segal | A61F 2/441 623/17.11 |
| 2009/0012621 | A1 * | 1/2009 | James | A61F 2/442 623/17.16 |
| 2009/0240341 | A1 * | 9/2009 | Diwan | A61F 2/4611 623/23.72 |
| 2009/0276048 | A1 * | 11/2009 | Chirico | A61B 17/025 623/17.11 |
| 2009/0281538 | A1 * | 11/2009 | Chong | A61B 18/1492 606/41 |
| 2009/0292323 | A1 * | 11/2009 | Chirico | A61B 17/8858 606/86 R |
| 2010/0036392 | A1 * | 2/2010 | Milijasevic | A61M 25/0043 606/129 |
| 2010/0145454 | A1 * | 6/2010 | Hoffman | A61F 2/447 623/17.12 |
| 2010/0168859 | A1 * | 7/2010 | Wardlaw | A61F 2/442 623/17.12 |
| 2011/0125158 | A1 * | 5/2011 | Diwan | A61F 2/441 606/93 |
| 2011/0153021 | A1 * | 6/2011 | Diwan | A61B 1/0125 623/17.16 |
| 2011/0208308 | A1 * | 8/2011 | Choi | A61F 2/441 623/17.16 |

* cited by examiner

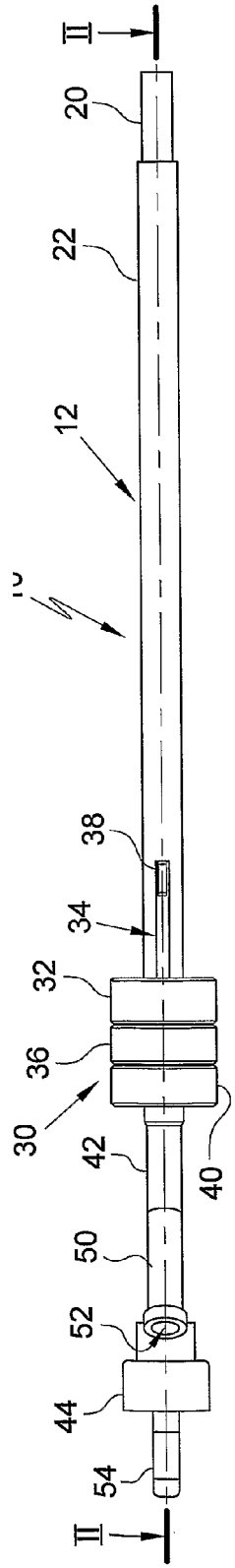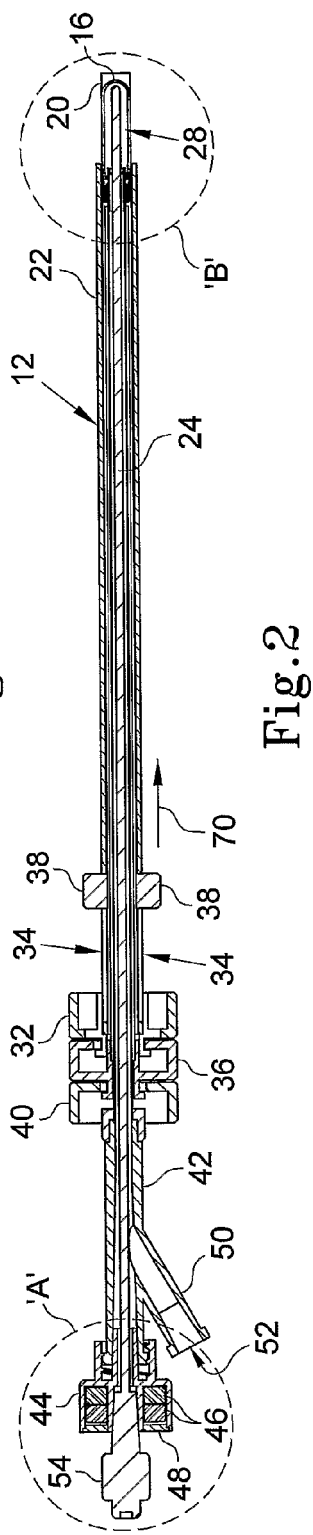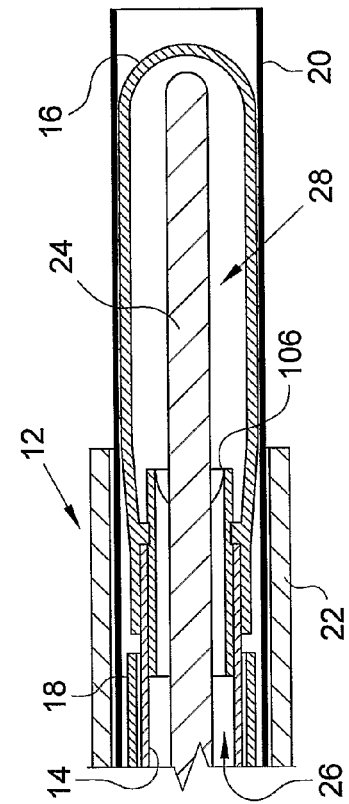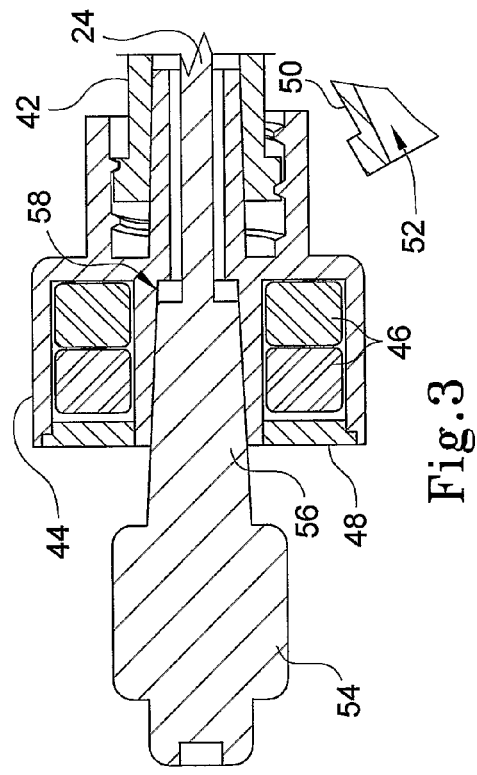
Fig.1
Fig.2
Fig.4
Fig.3

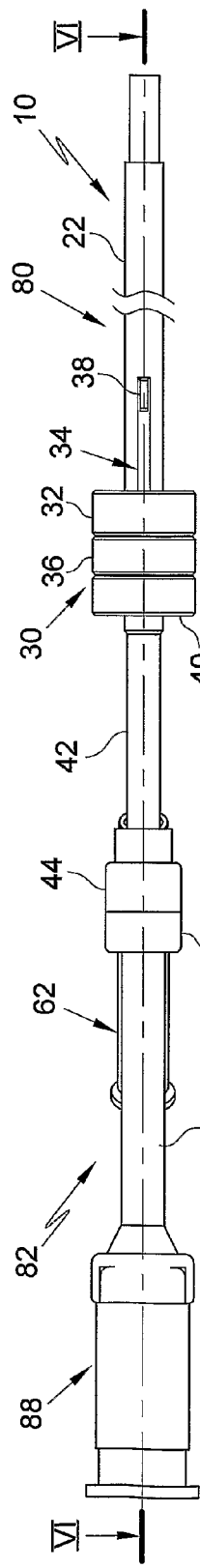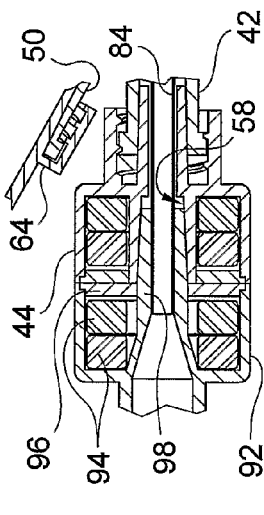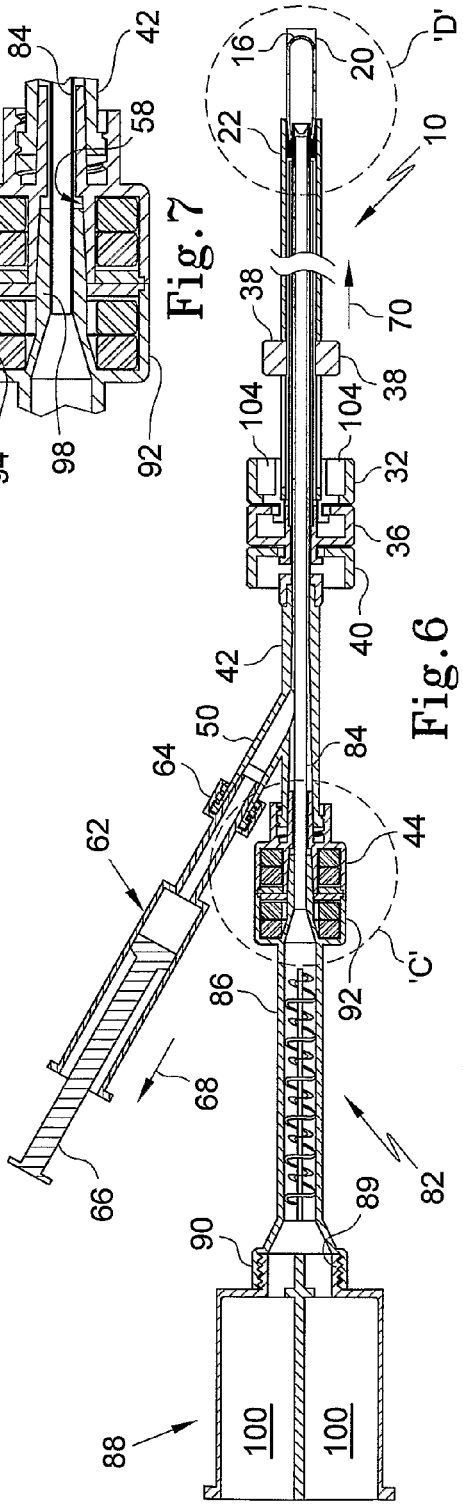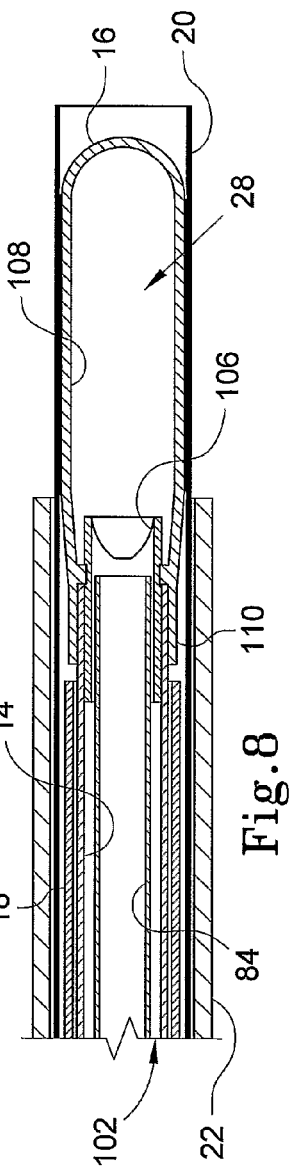
Fig. 5
Fig. 7
Fig. 6
Fig. 8

TISSUE PROSTHESIS INSERTION SYSTEM AND METHOD

CROSS-REFERENCE TO RELATED APPLICATIONS

The present application is a divisional patent application of U.S. patent application Ser. No.12,740,651 filed on May 13, 2011, now U.S. Pat. No. 8,728,161 issued on May 20, 2014, which is a national phase application under 35 U.S.C. §371 of International Patent Application No. PCT/AU2007/001657 filed on Oct. 31, 2007, the contents of which is incorporated herein by reference in its entirety.

FIELD

This invention relates, generally, to tissue prostheses and, more particularly, to a tissue prosthesis insertion system and to a method of forming a tissue prosthesis at a site in a patient's body. While the invention has particular application in the field of intervertebral disc nucleus replacement, the invention can be used in other tissue prosthesis insertion applications.

BACKGROUND

In the delivery of a prosthesis in a minimally invasive manner, use is made of a working cannula which is inserted through an incision in a patient's skin to the site to facilitate percutaneous delivery of the prosthesis to the site. A delivery mechanism is inserted into a lumen of the cannula for delivery of the prosthesis to the site. Generally, the cannula and the delivery mechanism are mounted on some form of structure such as a control device, a dispensing arrangement, or the like, For example, the cannula which helps dock the delivery system to the patient, in turn, can be docked to another fixed structure like the operating table using clamps so as to free the hands of the operator and to also provide stability while performing the device delivery. In addition, the cannula and the delivery mechanism are made as thin as possible so that the incision is made as small as possible.

In the case of a tissue prosthesis such as an intervertebral disc nucleus prosthesis, there is a need to perform an annulotomy on the annulus of the disc to gain access to an interior of the disc. The working cannula, after being inserted percutaneously, needs to be aligned with the opening formed in the annulus and retained in such alignment. It would therefore be advantageous to disturb the position of the cannula and the delivery device as little as possible and to keep the assembly as stable as possible,

SUMMARY

According to a first aspect of the invention, there is provided a tissue prosthesis insertion system which includes a first assembly comprising a plurality of nested tubes, one of the tubes being a carrier tube which, in use, receives a component of a tissue prosthesis at a distal end of the carrier tube; a magnetic mount carried at a proximal end of the first assembly; a second assembly removably attachable to the first assembly; and an attachment device carried at a distal end of the second assembly, the attachment device being responsive to the magnetic mount of the first assembly, the magnetic mount and the attachment device carrying complementary engaging formations to facilitate sealing between the magnetic mount and the attachment device.

The complementary engaging formations of the magnetic mount and the attachment device may comprise a Luer slip fitting. By "Luer slip fitting" is meant that one of the engaging formations comprises a tapered socket and the other of the engaging formations comprises a tapered fitting receivable in the tapered socket to form a hermetic seal between the fitting and the socket.

The magnetic mount of the first assembly may be a first magnetic mount and the attachment device may comprise a second magnetic mount which magnetically attaches to the first magnetic mount.

A stiffening member received within the first assembly, in use, projects into an interior of the component of the prosthesis, the stiffening member having a securing formation at its proximal end which engages the engaging formation of the magnetic mount in a sealing manner.

Further, the system may include a withdrawing device attachable to the first assembly, the withdrawing device, in use, being in communication with the interior of the component of the prosthesis and, with the stiffening member in position, creating a closed system so that operating the withdrawing device causes an increase in the volume of the closed system with a corresponding reduction in the pressure in the interior of the component, resulting in the component collapsing about the stiffening member.

The withdrawing device may be operable to test the integrity of the first assembly with the component mounted on the first assembly.

The first assembly may include a protective sheath, constituting one of the tubes of the first assembly, received over the component after it has been collapsed on to the stiffening member. At least one of the protective sheath and the component may be treated to facilitate sliding displacement between the protective sheath and the component. The treating of the protective sheath and/or the component may occur prior to inserting the first assembly into a working cannula used for insertion of the tissue prosthesis into position at a site in a patient's body. The treating may involve immersing the distal end of the first assembly in a lubricating fluid such as water. Instead, the treating may involve coating an inner surface of the protective sheath with a hygroscopic material or a hydrophilic material such as, for example, a hydrogel.

The protective sheath may have a distal end configured to facilitate sliding displacement of the protective sheath relative to the component of the prosthesis. More particularly, the distal end of the protective sheath may be configured by being bifurcated.

The protective sheath may include an operating member arranged' a proximal end to facilitate manipulation of the protective sheath.

The system may include the component, the component comprising an envelope of an elastically deformable material, the envelope defining an access opening with a flow control member being arranged in the access opening, the flow control member being configured to permit manipulation of fluid from an interior of the envelope prior to filling the envelope with a filler material. The flow control member may be a flow control valve which, in a rest condition, defines a withdrawal opening to allow withdrawal of the fluid from the interior of the envelope. The valve may be a duckbill valve having a pair of opposed operating flaps, the flaps being shaped so that, in their rest condition, they are spaced from each other to define the withdrawal opening.

The second assembly may comprise a filler tube received through the first assembly to communicate with the interior of the envelope and a filler material dispenser mountable to a proximal end of the filler tube. The dispenser assembly may feed into a static mixer, a distal end of the static mixer carrying the attachment device, the arrangement being such that, when the second assembly is fast with the first assembly and the withdrawing device is attached to the first assembly, a second closed system is created which enables fluid to be withdrawn from the interior of the envelope by the withdrawing device to create a low pressure region in the envelope. A "low" pressure is defined as a pressure below ambient pressure.

The dispenser may contain filler material, the filler material being of the same class or type of material as the material of the envelope so that, when the envelope has been charged with the filler material and the filler material has been allowed to set, a tissue prosthesis is formed which is elastically deformable. By "elastically deformable" is meant that the prosthesis can be deformed by the application of a force and, upon removal of the force, the tissue prosthesis returns to its undeformed state.

The system may include an obturating device receivable in one of the tubes of the first assembly for tamping a part of the tissue prosthesis into position after formation of the tissue prosthesis.

The obturating device may carry a locking member at its proximal end for locking to a working cannula of the system so that, after tamping of the part of the tissue prosthesis, the working cannula and the obturator can be removed simultaneously.

According to a second aspect of the invention, there is provided a tissue prosthesis insertion system which includes an assembly comprising a plurality of nested tubes, one of which is a carrier tube for carrying a component of a tissue prosthesis at its distal end and another of which is a filler tube received with clearance in the carrier tube to define a passage between the filler tube and the carrier tube, the distal end of the filler tube and the proximal end of the carrier tube being in sealing engagement; and a withdrawing device attachable to the assembly so that, when the withdrawing device is attached and the component of the tissue prosthesis is mounted on the distal end of the carrier tube, a closed system is formed which allows the withdrawing device to be used to increase the volume of the closed system to form a low pressure region at least in the component.

The assembly may comprise a stiffening member received in the carrier tube, a proximal end of the stiffening member and a proximal end of the assembly carrying complementary engaging formations for enabling the stiffening member to engage sealingly with at least one of the plurality of nested tubes to create an initial closed system, operation of the withdrawing device forming a low pressure region in the interior of the component, in use, to cause the component to collapse around the stiffening member. The system may include a filler tube insertable into the carrier tube after removal of the stiffening member to contribute to the formation of a further closed system which is then acted on by the withdrawing device to increase the volume of the closed system to reduce the pressure in the interior of the component.

The withdrawing device may be operable to test the integrity of the system to ensure that there are no leaks in the system.

According to a third aspect of the invention, there is provided a tissue prosthesis insertion system which includes a working cannula for accessing a site in a patient's body percutaneously in a minimally invasive manner for carrying out a tissue prosthesis insertion procedure at the site; and an obturating device receivable in the cannula for tamping a part of a tissue prosthesis into position after formation of the tissue prosthesis.

The obturating device may comprise a blunt-ended rod slidably receivable in the working cannula.

According to a fourth aspect of the invention, there is provided a tissue prosthesis component which includes an envelope of an elastically deformable material, the envelope defining an access opening; and a flow control member arranged in the access opening, the flow control member being configured to permit withdrawal of fluid from an interior of the envelope prior to filling the envelope with a filler material.

The flow control member may be a flow control valve which, in a rest condition, defines a withdrawal opening to allow the passage of fluid in both directions. The envelope may have a neck portion, the neck portion defining the access opening and the flow control member being arranged within the neck portion.

According to a fifth aspect of the invention, there is provided a method of preparing a first assembly of a tissue prosthesis system for insertion into a patient's body, the method comprising providing the first assembly which comprises a plurality of nested tubes, one of the tubes being a carrier tube; mounting a component of the prosthesis on a distal end of the carrier tube, the component being of an elastically deformable material; inserting a stiffening member into the first assembly so that the stiffening member extends into an interior of the component and causing a proximal end of the stiffening member to sealingly engage a proximal end of the first assembly; attaching a withdrawing device to the first assembly so that the withdrawing device is in fluid communication with the interior of the component; and operating the withdrawing device to reduce the pressure in the interior of the component to cause the component to collapse about the stiffening member.

The method may include attaching the withdrawing device to a fluid port of the first assembly in a sealing manner. The withdrawing device may be a syringe which is attached by a Luer lock mechanism to the fluid port of the first assembly.

After the component has been collapsed about the stiffening member, the method may include placing a protective sheath about the component. More particularly, the method may include placing the protective sheath about the component by sliding the protective sheath over the component, the protective sheath constituting one of the tubes of the nested tubes of the first assembly.

Further, the method may include treating one of the protective sheath and the component with a lubricating medium to facilitate relative displacement between the protective sheath and the component.

The method may include using the withdrawing device to test the integrity of the combination of the first assembly and the component and the stiffening member attached to the first assembly.

According to a sixth aspect of the invention, there is provided a method of forming a tissue prosthesis at a site in a patient's body, the method including providing a first assembly comprising a plurality of nested tubes, one of the tubes being a carrier tube with a component of the prosthesis carried at a distal end of the carrier tube; inserting the first assembly into a cannula placed in the patient's body; magnetically attaching a second assembly to a proximal end of the first assembly; and charging a filler material from the second assembly into the component and allowing the filler material to set.

The method may include, initially, preparing the first assembly as described above.

The method may include, once the distal end of the first assembly is at the desired location at the site in the patient's body, withdrawing the protective sheath to expose the component, the component being an envelope of an elastically deformable material.

The method may include removing the stiffening rod prior to magnetically attaching the second assembly to the first assembly. Further, the method may include causing the second assembly to engage sealingly with the first assembly so that, together with the component and the withdrawing device, a closed system is formed.

After the second assembly has been attached to the first assembly, the method may include operating the withdrawing device to create a low pressure in the component. Further, the method may include using the withdrawing device to test the integrity of the system comprising the two assemblies and the component attached to the first assembly.

The method may include dispensing the filler material from a dispenser of the second assembly. Preferably, the method includes purging filler material from the dispenser prior to attaching the dispenser to a static mixer constituting a part of the second assembly. The method may include, during filling of the component via a filler tube extending from the static mixer, operating the withdrawing device at least to maintain, or increase, the volume of the closed system.

The method may include, after filling the component, detaching the carrier tube from the tissue prosthesis formed by the combination of the component and the filler material contained in the component. The carrier tube may be detached prior to the filler material having cured or set or after the filler material has at least partially set. The method may include detaching the carrier tube from the tissue prosthesis when the required pressure has been reached in the component. In the case of an intervertebral disc nucleus prosthesis, the required pressure may be that which inhibits distraction of the disc.

In an embodiment, the method may include detaching tissue prosthesis by relative axial motion between the carrier tube and a displacement device of the first assembly. The displacement device may be a further tube arranged about the carrier tube and the relative axial motion may be effected by withdrawing the carrier tube relative to the displacement device. In another embodiment, the method may include detaching the tissue prosthesis by filling the component with filler material to the extent that the component is released from the carrier tube. In a further embodiment, the method may include detaching the tissue prosthesis by manipulating the carrier tube relative to the component to cause separation of a part of the component attached to the carrier tube from a remainder of the component, the separation occurring at a zone of weakness in the component. The manipulation may involve rotating the carrier tube with respect to the component.

The method may include, after formation of the tissue prosthesis, tamping a part of the tissue prosthesis into position.

If necessary or desirable, the method may include, before placing the component in position at the site, preparing the site. The method may include preparing the site by removing degenerative tissue from the site prior to placing the component at the site.

BRIEF DESCRIPTION OF DRAWINGS

FIG. 1 shows a plan view of a first assembly of a tissue prosthesis insertion system in accordance with an embodiment of the invention;

FIG. 2 shows a sectional side view of the first assembly of the system of FIG. 1 taken along line II-II in FIG. 1;

FIG. 3 shows a sectional side view, on an enlarged scale, of the part of the first assembly surrounded by circle 'A' in FIG. 2;

FIG. 4 shows a sectional side view, on an enlarged scale, of the part of the first assembly surrounded by circle 'B' in FIG. 2;

FIG. 5 shows a plan view of an assembly of the tissue prosthesis insertion system;

FIG. 6 shows a sectional side view of the assembly of the system taken along line VI-VI in FIG. 5;

FIG. 7 shows a sectional side view, on an enlarged scale, of the part of the assembly surrounded by circle 'C' in FIG. 6;

FIG. 8 shows a sectional side view, on an enlarged scale, of the part of the assembly surrounded by circle 'D' in FIG. 6;

DETAILED DESCRIPTION OF EXEMPLARY EMBODIMENTS

Figure 10:
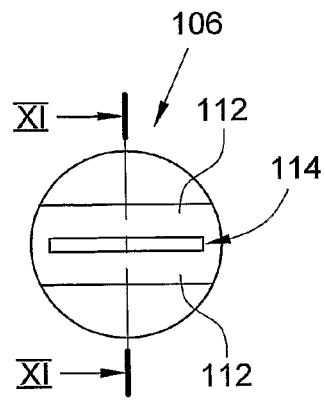
FIG. 10 shows an end view of the valve member.

Referring initially to FIGS., 1-4 of the drawings, a first assembly of a tissue prosthesis insertion system is illustrated and is designated generally by the reference numeral 10, The first assembly 10 comprises a plurality of nested tubes 12. As shown more clearly in Fig 4 or the drawings, the set of nested tubes 12 comprises an inner, carrier tube 14 on which a component, in the form of a filler valve 106 and an envelope 16 of a tissue prosthesis is mounted, the valve 106 being mounted on a distal end of the carrier tube 14. As best seen in FIG. 4, the carrier tube 14 is wedged between the envelope 16 and valve 106 and is received within a push-off tube 18 which is used for removing the envelope 16, after filling, from the carrier tube 14 as will be described in greater detail below.

The nested tubes 12 further include a protective sheath 20, arranged about the push-off tube 18. As illustrated most clearly in FIGS. 2 and 4 of the drawings, the protective sheath 20 is of a length to cover the envelope 16, the sheath 20 projecting beyond a distal end of the envelope 16 when in its operative, protective position. It is to be noted that the nested tubes 12 are shown, in use, mounted in a working cannula 22 used for inserting the first assembly 10 percutaneously to deliver the envelope 16 into a site at a patient's body in which the prosthesis is to be formed.

The nested tubes 12 are all preferably of a metal material such as a steel material which is bio-compatible.

The first assembly 10 further includes a stiffening member in the form of a stiffening rod 24, The stiffening rod 24 is of a length to project from a proximal end of the first assembly 10 through a lumen 26 (FIG. 4) of the carrier tube 14 to be received in an interior 28 of the envelope 16.

A collar assembly 30 is arranged at a proximal end of the nested tubes 12. The collar assembly 30 comprises a first collar 32 secured to a proximal end of the cannula 22. The cannula 22 has a pair of diametrically opposed, longitudinally extending slits, one of which is shown at 34 in FIG. 1 of the drawings, arranged distally of the collar 32. The protective sheath 20 is slidably arranged relative to the cannula 22 and has a pair of opposed, radially outwardly extending tabs 38 arranged at its proximal end. The tabs 38 project through the slits 34 in the cannula 22 to enable a clinician to manipulate the protective sheath 20.

The push-off tube 18 has a collar 36 arranged at its proximal end, the collar 36 being connected to the collar 32 of the cannula 22 via a bayonet fitting.

The carrier tube 14 carries a Y-connector 42 at its proximal end, the Y-connector 42 extending from a collar 40. The collar 40 attaches to the collar 36 of the push-off tube 18. The Y-connector 42 carriers a magnetic mount 44 at its proximal end. The magnetic mount 44 carries a plurality of annular magnets 46. These magnets 46 are rare earth magnets and are covered by a cover member 48.

The Y-connector 42 further includes a branch limb 50 defining a connection port 52 for a withdrawing device. The connection port 52 is in communication with a passage (not shown) defined between the carrier tube 14 and, initially, the stiffening rod 24.

The stiffening rod 24 carries a securing formation in the form of a mount 54 at its proximal end. A distal part 56 of the mount 54 is tapered and engages a tapered socket 58 defined by the magnetic mount 44 in a hermetically sealing manner so that, once a withdrawing device has been attached to the port 52, a closed system is formed.

More particularly, once the envelope 16 has been attached to the distal end of the carrier tube 14, the stiffening rod 24 is inserted through the lumen 26 of the carrier tube 14 to be received in the interior 28 of the envelope 16. When the distal end of the stiffening rod 24 is received in the envelope 16, the distal part 56 of the mount 54 of the stiffening rod 24 sealingly engages with the socket 58 in the magnetic mount 44 of the Y-connector 42 to form a hermetic seal.

A withdrawing device in the form of a syringe 62 (FIG. 6) is connected via a Luer fitting 64 to the port 52 of the Y-connector 42 to form a closed system. A plunger 66 of the syringe 62 is drawn in the direction of arrow 68. This increases the volume of the dosed system, reducing the pressure in the interior 28 of the envelope 16 and causing the envelope 16 to collapse about the distal end of the stiffening rod 24.

The tabs 38 of the protective sheath 20 are gripped by an operator assembling the first assembly 10 and are urged in the direction of arrow 70 (FIG. 2) to cause the protective sheath 20 to slide over and protect the envelope 16. To facilitate sliding movement between the protective sheath 20 and the envelope 16, a distal end of the first assembly 10 can be immersed in a suitable lubricating medium such as, for example, water. In this regard it should be noted that the envelope 16 is made of silicone material rendering it hydrophobic. Thus, the water acts as a lubricant and enables the protective sheath 20 to be slid over the envelope 16. Instead of immersing the distal end of the first assembly 10 in the lubricating medium, an internal surface of the protective sheath 20 could, optionally, be coated with a lubricating medium of a hygroscopic or hydrophilic material such as a hydrogel.

After retracting the sheath 20 in the direction opposite to that of arrow 70, the integrity of the first assembly 10 is tested for leaks by further withdrawing the plunger 66 of the syringe 62 in the direction of arrow 68. If the plunger 66 does not return to its previous position, this is an indication that there is a leak in the first assembly 10 and remedial action can be taken to locate the leak. Conversely, should the plunger 66 return to its previous position, this is an indication that the integrity of the first assembly 10 is intact and the procedure can proceed.

Instead of pulling on the plunger 66 of the syringe 62, testing of the integrity of the first assembly 10 could involve pushing on the plunger 66 of the syringe 62 and then releasing the plunger 66. If the plunger 66 does not return to its original position that is an indication that there is a leak in the system such as may occur if the envelope 16 is torn.

Referring now to FIGS. 5-8 of the drawings, a tissue prosthesis insertion system is shown in greater detail and is designated generally by the reference numeral 80. The system 80 includes the first assembly 10 and a second assembly 82. The second assembly 82 comprises a filler tube 84 including a static mixer 86 at a proximal end of the filler tube 84. The static mixer 86 is secured to a distal end of a filler material dispenser 88. The filler material dispenser 88 has a screw-threaded attachment 89 for engaging a screw-threaded boss 90 at a proximal end of the static mixer 86.

A distal end of the static mixer 86 carries an attachment device in the form of a second magnetic mount 92. As illustrated more clearly in FIG. 7 of the drawings, the magnetic mount 92 comprises a pair of annular rare earth magnets 94 closed off by a cover 96. The mount 92 also includes a tapered fitting 98. The tapered fitting 98 of the mount 92 and the tapered socket 58 of the mount 44 define complementary engaging formations. Thus, the tapered fitting 98 is received within the socket 58 of the magnetic mount 44 of the Y-connector 42 in a hermetically sealing manner, the fitting 98 and the socket 58 constituting a Luer slip fitting. Thus, once again, once the syringe 62 has been attached to the port 52 of the Y-connector 42, a closed system is formed.

The benefit of magnetically attaching the second assembly 82 to the first assembly 10 is that the requirement for relative rotation between the two assemblies 10 and 82 for attachment to each other is obviated. This also enables the cannula 22 of the first assembly 10 more accurately to be retained in position, in use. It also maintains the engagement of the two assemblies 10 and 82 during filling of the envelope 16 as will be discussed in greater detail below.

The filler material used for forming the tissue prosthesis is a silicone rubber material. To inhibit curing of the filler material prior to its being charged into the envelope 16, the filler material is retained in two, separate parts. For this purpose, the dispenser 88 includes two separate reservoirs 100, in each of which one part of the filler material is initially received. Each reservoir 100 has a plunger (not shown) associated with it for dispensing the parts of the filler material simultaneously from the reservoirs 100 into the static mixer 86 where the parts are mixed prior to being charged into the filler tube 84 to be injected into the interior 28 of the envelope 16. The plungers are displaceable together with each other via a suitable displacing device (also not shown), for example, a pneumatic gun.

After removal of the stiffening rod 24, the second assembly 82 is attached to the first assembly 10 via the magnetic mounts 44 and 92. More particularly, the part of the second assembly 82 comprising the static mixer 86 with the filler tube 84 projecting from the static mixer 86 is magnetically attached to the first assembly 10 via the magnetic mounts 44 and 92 with the fitting 98 sealingly engaging in the socket 58. Prior to attaching the dispenser 88 to the static mixer 86, filler material is purged from the reservoirs 100 by urging the plungers towards the threaded end 89 of the dispenser 88 to expel a portion of filler material from the reservoirs 100 to ensure that the correct ratio of the two parts of the filler material is dispensed. The dispenser 88 is then attached to the static mixer 86.

The pressure in the interior 28 of the envelope 16 is again lowered by withdrawing the plunger 66 of the syringe 62 in the direction of arrows 68. This serves to collapse the envelope 16 prior to the filler material being charged via the filler tube 84 into the interior 28 of the envelope 16. To enable the pressure in the interior 28 of the envelope 16 to be lowered, the filler tube 84 is a loose fit within the carrier tube 14 to create an annular passage 102 (FIG. 8) via which air can be withdrawn from the interior 28 of the envelope 16 by the syringe 62.

After lowering the pressure in the interior of the envelope 16, the integrity of the system 80 is again checked by further attempting to withdraw the plunger 66 from the syringe 62 in the direction of the arrows 68. Should the plunger 66 remain in its withdrawn position, this is an indication that there is a leak in the system and remedial action can be taken to locate the leak. Conversely, should the plunger 66 return to its previous position, this is an indication that the integrity of the system 80 is intact and the clinician can proceed. Once again, instead of pulling the plunger 66, testing could involve pushing the plunger 66 and determining whether or not it returns to its original position. If not, that is an indication that there is a leak in the system 80 and remedial action can be taken to locate the leak.

The use of the system 80 will be described with reference to its application in the formation of an intervertebral disc nucleus prosthesis. An intervertebral disc 124 (FIGS. 12 & 13) comprises an annular part called the annulus fibrosis, or annulus, 126. The annulus 126 surrounds a nucleus pulposus (not shown). The intervertebral disc 124 cooperates with end plates of vertebrae 128 between which the disc 124 is sandwiched. When the disc 124 degenerates, there is a tendency for nuclear material to extrude through the annulus 126 reducing the efficacy of the disc 124. Should the degeneration be detected at a sufficiently early stage, the disc 124 can be restored by replacing the natural nucleus pulposus with a prosthetic disc nucleus 130.

The applicant has developed a synthetic disc nucleus comprising an envelope 16 of a silicone material with a filler material of a similar silicone material. When the filler material has been injected into the envelope 16 and it has been allowed to set, a uniform, integral structure is formed which at least partially restores the biomechanics of the disc. More particularly, the nucleus prosthesis is elastically deformable. Thus, the application of force will cause the nucleus prosthesis to deform elastically so that, once the force has been removed, the prosthesis will return to its relaxed, unreformed state. The prosthesis is described in greater detail in the applicant's International Patent Application No. PCT7AU2006/001176 entitled "A tissue prosthesis and a method of, and equipment for, forming a tissue prosthesis" filed on 15 Aug. 2006. The contents of that International Patent Application are incorporated by reference in this specification in their entirety.

To insert the nucleus prosthesis into the disc, an incision in made in the patient's skin and an annulotomy is performed on the annulus 126 of the disc 124 in a minimally invasive manner to form an opening 132. This enables access to be gained to the interior of the disc 124. To perform the annulotomy, the cannula 22 is inserted through the incision until a distal ends abuts the annulus 126. An annulotomy performing tool, such as a trocar or a guide wire plus dilator (not shown), is inserted through the cannula 22 and pierces the annulus 126 to enable access to be gained to the nuclear material of the disc 124. If necessary, a nucleotomy is performed to remove the nuclear material. However, in certain circumstances, the degenerative process may have dehydrated, extruded or shrunken the nuclear material so that a cavity has already been formed and the necessity to perform the nucleotomy is obviated.

Whether or not a nucleotomy is performed, once the cavity in the disc 124 is present, the first assembly 10 is inserted into the cannula 22. As indicated above, the first assembly 10 comprises the carrier tube 14 with the envelope 16 mounted on a distal end of the carrier tube 14, the push-off tube 18 and the protective sheath 20, with the protective sheath 20 extending over the envelope 16.

Once the envelope 16 is in position within the disc 124, the protective sheath 20 is withdrawn by urging the tabs 38 of the protective sheath 20 in the direction opposite to that of the arrow 70, the tabs 38 being received within recesses 104 of the collar 32 of the cannula 22.

The assembly 10 is locked in position relative to the working cannula 22 by the bayonet fitting of the collar 36 of the push-off tube 18 engaging the collar 32 of the cannula 22.

The stiffening rod 24 is removed and the second assembly 82 is attached to the first assembly 10, as previously described. Some filler material is purged from the reservoirs 100 of the dispenser 88 and the dispenser 88 is then attached to the proximal end of the static mixer 86. This re-forms the dosed system enabling air to be removed from the envelope 16 by operating the syringe 62 and pulling its plunger 66 in the direction of arrows 68.

The plungers of the dispenser 88 are then urged towards the distal end of the dispenser 88 to discharge material from the reservoirs 100. The parts of the filler material discharged from the reservoir 100 are mixed together in the static mixer 86 before being fed into the filler tube 84. The plunger 66 of the syringe 62 is continued to be withdrawn in the direction of arrow 68 during passage of the filler material along the filler tube 84 at least to maintain or to increase the volume of the dosed system to remove air from the envelope 16 as the filler material is charged into the envelope 16. The filler material 84 is conveyed through the filler tube 84 into the interior 28 of the envelope 16 through a tissue prosthesis component in the form of a filler valve 106. The filler valve 106 will be described in greater detail below.

As the filler material enters the interior 28 of the envelope 16, it causes the envelope 16 to expand to conform to the shape of the cavity within the intervertebral disc. It will be appreciated that, due to the resilient flexibility of the envelope 16, the envelope 16 will readily conform to the shape of the cavity and the envelope 16 need not be of any pre-configured dimensions.

Figure 11:
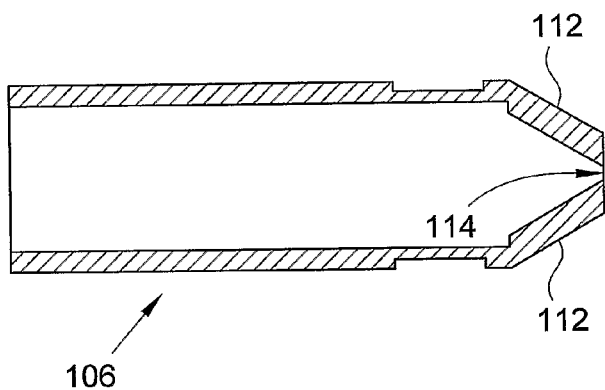
FIG. 11 shows a sectional side view of the valve member taken along line XI-XI in FIG. 10.
Figure 9:
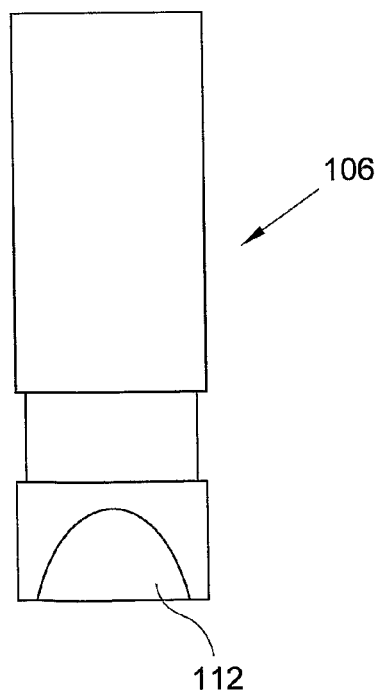
FIG. 9 shows a plan view of a valve member forming part of a tissue prosthesis of the system.

Referring now to FIGS. 9-11 of the drawings, the tissue prosthesis component in the form of the filler valve 106 of the envelope 16 is described in greater detail. It is to be noted that the envelope 16 has a bulbous body portion 108 (FIG. 8) integrally formed with a neck portion 110. The envelope 16 is attached to the distal end of the carrier tube 14 via the neck portion 110. The valve 106 is received within the neck portion 110 of the envelope 16. The valve 106 is a duck bill valve having a pair of opposed operating members or operating flaps 112. The operating flaps 112, when in their rest condition, as shown in FIGS. 9-11 of the drawings, do not close fully and a slit 114 is defined between the operating flaps 112 of the valve 106. This is desirable so that, prior to filler material being charged into the interior 28 of the envelope 16, air can be withdrawn from the interior 28 of the envelope 16 via the slit 114 using the syringe 62.

Once the filler material has filled the interior 28 of the envelope 16, it occludes the slit 114 or, instead, presses down on the operating flaps 112 to cause them to deform to close the slit 114. Also, the filler material could have sufficient viscosity to inhibit extrusion of the filler material outwardly through the slit 114. It will be appreciated that, once the filler material has set, it no longer matters whether or not the slit 114 is fully closed.

To inhibit overfilling of the envelope 16, the envelope is mounted on the carrier tube 14 such that as the envelope 16 fills with filler material, any excess filler material will "extrude" between the neck portion 110 of the envelope 16 and the carrier tube 14 causing the envelope 16 to be released from the carrier tube 14.

After the desired quantity of filler material has been charged into the envelope 16, the second assembly 82 is detached from the first assembly 10 by breaking the magnetic bond between the magnetic mounts 44 and 92. The filler tube 84 is withdrawn from the interior of the carrier tube 14.

The envelope 16 is detached from the carrier tube 14 by relative displacement between the carrier tube 14 and the push-off tube 18. More particularly, the carrier tube 14 is withdrawn from the push-off tube 18 by detaching the collar 40 of the Y-connector 42 from the collar 36 of the push-off tube 18 and withdrawing the carrier tube 14. This causes the proximal end of the neck portion 110 of the envelope 16 to come into abutment with the distal end of the push-off tube 18 causing detachment of the envelope 16 from the carrier tube 14. The push-off tube 18 is then removed. The tissue prosthesis 134 (FIGS. 12 & 13), comprising the envelope 16 filled with the filler material, is retained in position within the intervertebral disc 124 of the patient.

Figure 12:
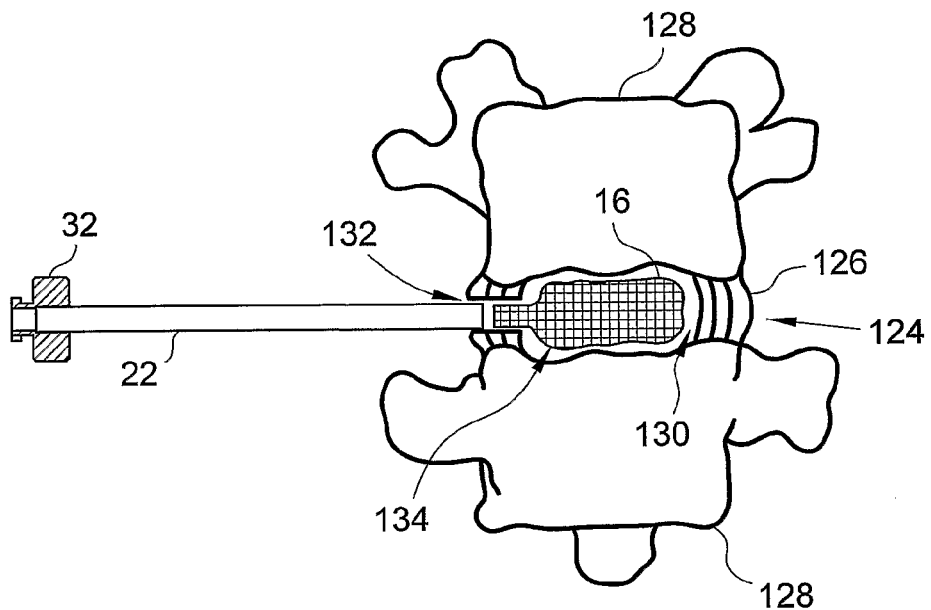
FIG. 12 shows a schematic side view of a working cannula of the assembly in position after formation of the tissue prosthesis.
Figure 13:
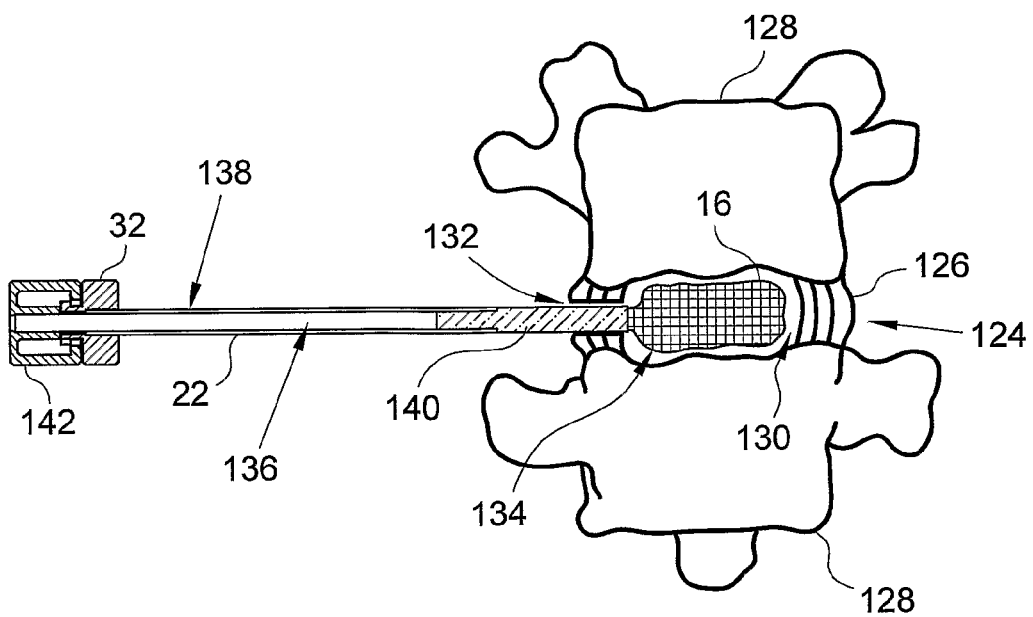
FIG. 13 shows a schematic side view of a further part of the system inserted into the cannula to complete formation of the tissue prosthesis.

As shown in greater detail in FIGS. 12 and 13 of the drawings, after removal of the carrier tube 14, at least a part of the neck portion 110 of the envelope 16 may protrude through the annulus 126 of the intervertebral disc 124. In addition a residue of filler material may be present in the distal end of the working cannula 22. Therefore, prior to removal of the working cannula 22, an obturator 136 is inserted into a lumen 138 of the cannula 22. The obturator 136 comprises a blunt-ended rod 140 which is a tight fit within the lumen 138 of the cannula 22.

The obturator 136 is used to urge any residue of filler material into the disc cavity and to tamp the part of the neck portion 110 of the envelope 16 into the disc cavity, as shown in FIG. 13 of the drawings. The prosthesis 134 is thus entirely contained within the disc cavity 134 with minimal, if any, protrusion into the annulus 126 of the disc 124.

The obturator 136 can, if desired, be locked to the working cannula 22 by an attachment collar 142 carried at a proximal end of the obturator 136 locking to the collar 32 of the working cannula 22 in a bayonet fitting manner. This allows the obturator 136 to be retained in position during setting of the filler material and inhibits extrusion of filler material from the envelope 16 and/or from the disc cavity.

After completion of the tamping and setting process, the working cannula 22 and the obturator 136 are removed.

Tamping the neck portion 110 of the envelope 16 into the disc cavity 122 inhibits prosthesis expulsion and excessive loading on the aperture 132 in the annulus 126 of the disc 124. In addition, the fact that there is no remnant of the envelope 16 in the annulus 124 enhances closure of the aperture 132 in the annulus 124.

It is an advantage of the invention that a tissue prosthesis insertion system is provided which is simple to operate by a clinician. The assemblies are easily connected together using the magnetic connection which improves the stability of the device and obviates the need for relative rotation of the assemblies relative to one another to connect them together. In addition, the use of the protective sheath protects the envelope against damage while it is being inserted into and positioned in the patient's body. The sheath is relatively simple to operate by the clinician thereby improving the performance of the system as a whole. Further, the use of the syringe as a low pressure generating device simplifies the system and precludes the need for complicated pumps, etc. Also, due to the fact that the syringe provides a closed system, it is not necessary to continuously withdraw air out of the envelope while it is being charged with filler material. This further simplifies operation of the system.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A tissue prosthesis insertion system, comprising:
    an assembly including a plurality of nested tubes, one of which is a carrier tube for carrying a component of a tissue prosthesis at its distal end and another of which is a filler tube received with clearance in the carrier tube to define a passage between the filler tube and the carrier tube;
    wherein, the distal end of the filler tube and the proximal end of the carrier tube are configured to facilitate engagement with each other;
    a withdrawing device attachable to the assembly so that, when the withdrawing device is attached and the component of the tissue prosthesis is mounted on the distal end of the carrier tube, a closed system is formed which allows the withdrawing device to be used to increase a volume of the closed system to form a low pressure region at least in the component; and
    a first and second magnetic mount, wherein the first magnetic mount is carried at a proximal end of the assembly and wherein the second magnetic mount is carried at a distal end of an another assembly, wherein said set of magnets and said another set of magnets are arranged relative to one another to help maintain a coupling engagement between said assembly and said another assembly and to substantially negate a need for relative rotational movement between the assembly and the another assembly during disengagement from one another, such that the another assembly is used to dispense a filler material to the assembly.

2. The tissue prosthesis insertion system according to claim 1, wherein said assembly further includes:
    a stiffening member received in the carrier tube, a proximal end of the stiffening member and a proximal end of the assembly carrying complementary engaging formations for enabling the stiffening member to engage sealing with at least one of the plurality of nested tubes to create an initial closed system, operation of the withdrawing device forming a low pressure region in an interior of the component, in use, to cause the component to collapse around the stiffening member.

3. The tissue prosthesis insertion system according to claim 2, wherein said filler tube is insertable into the carrier tube after the removal of the stiffening member to contribute to the formation of a further closed system which is then acted on by the withdrawing device to increase the volume of the closed system to reduce pressure in the interior of the component.

4. The tissue prosthesis insertion system according to claim 3, wherein said plurality of nested tubes includes:
    a working cannula having a pair of diametrically opposed longitudinally extending cannula slits, said working cannula being dimensioned for receiving therein said carrier tube and said filler tube to facilitate the percutaneous delivery of the component to an implant site in a body of a patient.

5. The tissue prosthesis insertion system according to claim 4, wherein said plurality of nested tubes further includes a push off tube dimensioned for receiving therein said carrier tube;
said push off tube having arranged thereabout a protective sheath with a sufficient length to cover and project beyond a distal end of the component when in an operative position for delivery to the implant site.

6. The tissue prosthesis insertion system according to claim 5,
wherein said first magnetic mount includes a set of annular magnets and a tapered socket; and
wherein said second magnetic mount includes another set of annular magnets and a tapered fitting dimensioned to be received within said tapered socket in a hermetically sealing manner sealing said assembly to said another assembly; and
wherein said set of annular magnets and said another set of annular magnets are arranged relative to one another to help maintain a coupling engagement between said assembly and said another assembly and to substantially prevent rotational movement between the assembly and the another assembly during disengagement from one another.

7. The tissue prosthesis insertion system according to claim 6, wherein said tapered fitting and said tapered socket define a Luer slip fitting.

8. The tissue prosthesis insertion system according to claim 2, wherein said plurality of nested tubes includes:
a working cannula having a pair of diametrically opposed longitudinally extending cannula slits, said working cannula being dimensioned for receiving therein said carrier tube and said filler tube to facilitate the percutaneous delivery of the component to an implant site in a body of a patient.

9. The tissue prosthesis insertion system according to claim 8, wherein said plurality of nested tubes further includes a push off tube dimensioned for receiving therein said carrier tube;
said push off tube having arranged thereabout a protective sheath with a sufficient length to cover and project beyond a distal end of the component when in an operative position for delivery to the implant site.

10. The tissue prosthesis insertion system according to claim 9,
wherein said first magnetic mount includes a set of annular magnets and a taperedsocket; and
wherein said second magnetic mount includes another set of annular magnets and a tapered fitting dimensioned to be received within said tapered socket in a hermetically sealing manner sealing said assembly to said another assembly; and
wherein said set of annular magnets and said another set of annular magnets are arranged relative to one another to help maintain a coupling engagement between said assembly and said another assembly and to substantially prevent rotational movement between the assembly and the another assembly during disengagement from one another.

11. The tissue prosthesis insertion system according to claim 10, wherein said tapered fitting and said tapered socket define a Luer slip fitting.

12. The tissue prosthesis insertion system according to claim 3, wherein said withdrawing device is operable to test the integrity of the system; and wherein said component is a component valve assembly.

13. The tissue prosthesis insertion system according to claim 2, wherein said withdrawing device is operable to test the integrity of the system; and wherein said component is a component valve assembly.

14. The tissue prosthesis insertion system according to claim 1, wherein said plurality of nested tubes includes:
a working cannula having a pair of diametrically opposed longitudinally extending cannula slits, said working cannula being dimensioned for receiving therein said carrier tube and said filler tube to facilitate the percutaneous delivery of the component to an implant site in a body of a patient.

15. The tissue prosthesis insertion system according to claim 14, wherein said plurality of nested tubes further includes a push off tube dimensioned for receiving therein said carrier tube; said push off tube having arranged thereabout a protective sheath with a sufficient length to cover and project beyond a distal end of the component when in an operative position for delivery to the implant site.

16. The tissue prosthesis insertion system according to claim 15,
wherein said first magnetic mount includes a set of annular magnets and a tapered socket; and
wherein said second magnetic mount includes another set of annular magnets and a tapered fitting dimensioned to be received within said tapered socket in a hermetically sealing manner sealing said assembly to said another assembly.

17. The tissue prosthesis insertion system according to claim 16, wherein said tapered fitting and said tapered socket define a Luer slip fitting.

18. The tissue prosthesis insertion system according to claim 1, wherein said withdrawing device is operable to test the integrity of the system; and wherein said component is a component valve assembly.

19. A tissue prosthesis insertion system, comprising:
an assembly including a plurality of nested tubes, one of which is a carrier tube for carrying a component of a tissue prosthesis at about its distal end and another of which is a filler tube received with clearance in the carrier tube to define a passage between the filler tube and the carrier tube;
wherein, the distal end of the filler tube and the proximal end of the carrier tube are configured to facilitate engagement with each other;
a withdrawing device attachable to the assembly so that, when the withdrawing device is attached and the component of the tissue prosthesis is mounted on the distal end of the carrier tube, a closed system is formed which allows the withdrawing device to be used to increase a volume of the closed system to form a low pressure region at least in the component;
a withdrawing device attachable to the assembly so that, when the withdrawing device is attached and the component of the tissue prosthesis is mounted on the distal end of the carrier tube, a closed system is formed which allows the withdrawing device to be used to increase the volume of the closed system to form a low pressure region at least in an envelope;
a stiffening member received in the carrier tube, a proximal end of the stiffening member and a proximal end of the assembly carrying complementary engaging formations for enabling the stiffening member to engage sealing with at least one of the plurality of nested tubes to create an initial closed system, operation of the withdrawing device forming a low pressure region in an interior of the component, in use, to cause the component to collapse around the stiffening member;

wherein said filler tube is insertable into the carrier tube after the removal of the stiffening member to contribute to the formation of a further closed system which is then acted on by the withdrawing device to increase the volume of the closed system to reduce pressure in the interior of the component; and a first and second magnetic mount, wherein the first magnetic mount is carried at a proximal end of the assembly and the second magnetic mount is carried at a distal end of an another assembly, wherein said set of magnets and said another set of magnets are arranged relative to one another to help maintain a coupling engagement between said assembly and said another assembly and to substantially negate a need for relative rotational movement between the assembly and the another assembly during disengagement from one another, such that the another assembly is used to dispense a filler material to the assembly.

20. The tissue prosthesis insertion system according to claim 19, further comprising:

wherein said first magnetic mount includes a set of annular magnets and a tapered socket; and wherein said second magnetic mount includes another set of annular magnets and a tapered fitting dimensioned to be received within said tapered socket in a hermetically sealing manner sealing said assembly to said another assembly; and wherein said tapered fitting and said tapered socket define a Luer slip fitting.

* * * * *